(12) United States Patent
Ogura et al.

(10) Patent No.: US 11,284,863 B2
(45) Date of Patent: Mar. 29, 2022

(54) SURFACE PROPERTY MEASUREMENT METHOD, SURFACE PROPERTY MEASUREMENT APPARATUS, AND RECORDING MEDIUM

(71) Applicants: SHISEIDO COMPANY, LTD., Tokyo (JP); NATIONAL UNIVERSITY CORPORATION TOYOHASHI UNIVERSITY OF TECHNOLOGY, Aichi (JP); HONDA ELECTRONICS CO., LTD., Aichi (JP)

(72) Inventors: Yuki Ogura, Kanagawa (JP); Naohiro Hozumi, Aichi (JP); Sachiko Yoshida, Aichi (JP); Kazuto Kobayashi, Aichi (JP); Yusuke Hara, Kanagawa (JP)

(73) Assignees: SHISEIDO COMPANY, LTD., Tokyo (JP); NATIONAL UNIVERSITY CORPORATION TOYOHASHI UNIVERSITY OF TECHNOLOGY, Aichi (JP); HONDA ELECTRONICS CO., LTD., Aichi (JP)

( * ) Notice: Subject to any disclaimer, the term of this patent is extended or adjusted under 35 U.S.C. 154(b) by 989 days.

(21) Appl. No.: 15/763,301

(22) PCT Filed: Sep. 13, 2016

(86) PCT No.: PCT/JP2016/076973
§ 371 (c)(1),
(2) Date: Mar. 26, 2018

(87) PCT Pub. No.: WO2017/056968
PCT Pub. Date: Apr. 6, 2017

(65) Prior Publication Data
US 2019/0059857 A1 Feb. 28, 2019

(30) Foreign Application Priority Data

Sep. 29, 2015 (JP) .................................. 2015-192075
Sep. 8, 2016 (JP) .............................. JP2016-175317

(51) Int. Cl.
*A61B 8/08* (2006.01)
*A61B 8/00* (2006.01)
(Continued)

(52) U.S. Cl.
CPC ............ *A61B 8/485* (2013.01); *A61B 8/0858* (2013.01); *A61B 8/5238* (2013.01); *A61B 8/587* (2013.01);
(Continued)

(58) Field of Classification Search
None
See application file for complete search history.

(56) References Cited

U.S. PATENT DOCUMENTS 6,682,486 B2 * 1/2004 Ogawa .................. A61B 8/00
600/443
2007/0250294 A1 10/2007 Omata et al.

FOREIGN PATENT DOCUMENTS

JP H04-071533 3/1992
JP 2006-271765 10/2006
(Continued)

OTHER PUBLICATIONS

International Search Report for PCT/JP2016/076973 dated Nov. 29, 2016.

*Primary Examiner* — Amelie R Davis
*Assistant Examiner* — Marjan Saboktakin
(74) *Attorney, Agent, or Firm* — Ipusa, PLLC

(57) ABSTRACT

A surface property measurement technology by which a surface property of a substance can be evaluated with high accuracy, is provided.

(Continued)

A surface property measurement method includes radiating an ultrasonic wave to a measurement target and acquiring a reflected signal from the measurement target; calculating, by a measurement apparatus, a maximum value of a cross-correlation function between the reflected signal from the measurement target and a reference reflected signal from a reference substance acquired in advance; calculating a reflection component at an interface, by using the maximum value of the cross-correlation function; and outputting, as a measurement value, one of an acoustic impedance of the measurement target or an acoustic impedance of the reference substance, according to a result of comparing the reflection component with the reference reflected signal.

11 Claims, 12 Drawing Sheets

(51) Int. Cl.
    *G01N 29/09*     (2006.01)
    *G01N 29/04*     (2006.01)
    *G01N 29/50*     (2006.01)
    *G01N 29/11*     (2006.01)
    *G01N 29/44*     (2006.01)
    *G01N 29/46*     (2006.01)

(52) U.S. Cl.
    CPC ............ *G01N 29/041* (2013.01); *G01N 29/09* (2013.01); *G01N 29/11* (2013.01); *G01N 29/4436* (2013.01); *G01N 29/46* (2013.01); *G01N 29/50* (2013.01); *A61B 8/4427* (2013.01); *G01N 2291/015* (2013.01); *G01N 2291/044* (2013.01)

(56) References Cited

FOREIGN PATENT DOCUMENTS

| | | | |
|---|---|---|---|
| JP | 2006271765 A | * | 10/2006 |
| JP | 2007-271765 | | 10/2007 |
| WO | 2005/100951 | | 10/2005 |

* cited by examiner

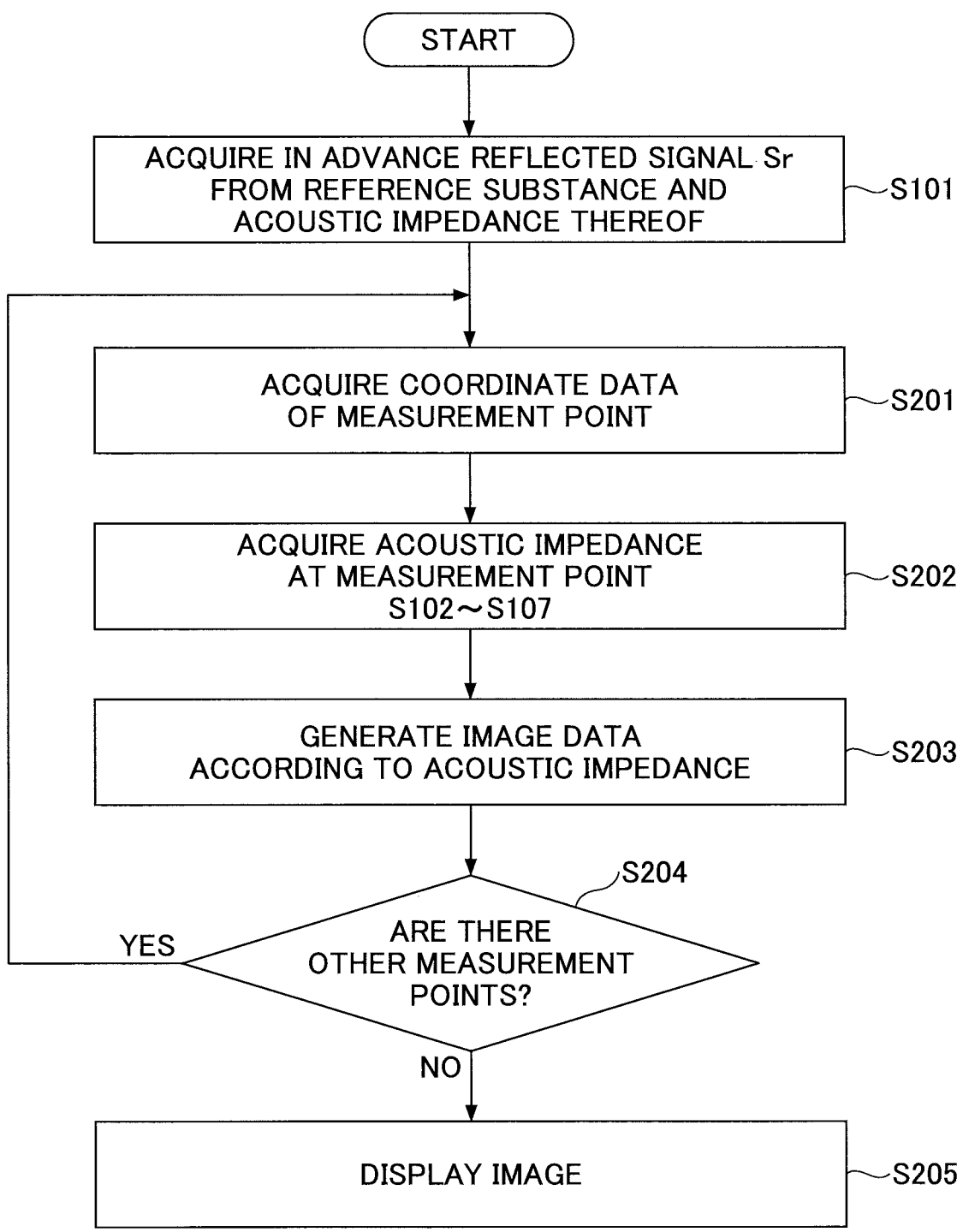

SURFACE PROPERTY MEASUREMENT METHOD, SURFACE PROPERTY MEASUREMENT APPARATUS, AND RECORDING MEDIUM

TECHNICAL FIELD

The present invention relates to measurement of surface properties, and in particular, to measurement of physical properties of a surface and/or surface layer of an object by using ultrasonic waves.

BACKGROUND ART

Evaluation of the properties of a surface and/or surface layer of an object is useful in various fields. For example, in the case of a living body, the skin exists on the surface and/or surface layer of the living body, and by recognizing the skin quality that is a property of the skin, it is possible to perform skin care according to the skin quality and maintain healthy skin. In the field of beauty and cosmetics, the skin quality is generally evaluated according to inquiries by a beauty technician, etc. Furthermore, dynamic properties of the skin (skin flexibility and elasticity, etc.) and optical properties of the skin (skin luster and transparency, etc.) have been measured by using measuring instruments, and skin conditions and functions have been objectively evaluated.

Conventional methods of measuring the physical properties of skin by using a noninvasive measuring instrument, are generally performed by applying stress on the surface of the skin under constant conditions, and by measuring the reaction force or response after applying constant displacement. The values obtained by these measurement methods have been detected as evaluation values of physical properties of the entire skin. However, the property value is detected as a value including all contributions of the respective layers constituting the skin (horny cell layer, epidermis, dermis, and subcutaneous tissue). Since each layer constituting the skin has its own role and function, it is desirable that each layer can be individually measured and evaluated.

In particular, the horny cell layer at the outermost layer of the skin has a barrier function and a moisturizing function necessary for maintaining life activities, and therefore accurate measurement of property values of the horny cell layer is an important task in the medical and pharmaceutical fields. Furthermore, the object that can be appealed in skin care is limited to the horny cell layer in terms of pharmaceutical affairs, and therefore the property evaluation of only the horny cell layer is also meaningful in the field of beauty and cosmetics. However, by the conventional stress/displacement application type noninvasive skin measuring instrument, it has been impossible to measure the physical properties of only the horny cell layer. In order to measure the physical property value of each layer of the skin, it has been necessary to use an invasive technique using a cut skin piece of a biopsy, etc., instead of the noninvasive technique. For example, the method of Patent Literature 1 is a method of measuring a sound velocity distribution of a skin cross-section by preparing a tomographic sample of the skin. By this method, it is possible to measure the hardness of each region of the skin by the sound velocity of each layer of the skin tomography, that is, the physical property value that is an index of the volume elasticity.

FIG. 1 is a sound velocity distribution image of a cross-section of a skin piece cut by a conventional method. Image (A) of FIG. 1 illustrates a skin piece of the cheek of a young person, and an image (B) of FIG. 1 illustrates a cross-section of a skin piece of the cheek of an elderly person. As illustrated in FIG. 1, it is known that complex variations can be observed; specifically, in the skin (cheek) exposed to ultraviolet rays, the sound velocity in the horny cell layer at the outermost layer is high (hard), while the sound velocity, that is, the volume elasticity in the middle layer of the dermis decreases (softens). With regard to the measurement target in which such complex variations are observed, it is impossible to evaluate the physical properties of only the surface and/or surface layer, by conventional noninvasive skin measuring instruments of the stress/displacement application type. By actually evaluating the skin (cheek) exposed to ultraviolet rays, with a skin viscoelasticity measuring device by the suction method (a method of evaluating the height of the skin floating up when the skin is depressurized with constant pressure), which is widely used as a noninvasive skin measuring instrument, the influence of the softening of the dermis is applied largely to the evaluation results, and it is not possible to capture the phenomenon of the surface and/or surface layer becoming hard.

Note that other than conventional noninvasive skin measuring instruments based on stress/displacement application, in recent years, there has been proposed a technique for noninvasively obtaining hardness information at different depths of the skin, by using ultrasonic waves (Patent Literature 2). In this method, information of a plurality of layers at different depths is measured by radiating ultrasonic waves including different frequency components to the skin, and calculating the acoustic impedance of the reflected waves. It is possible to distinguish between the information from the inside of the skin and the information of the skin surface and/or surface layer, and it is possible to obtain physical properties only of the skin surface and/or surface layer.

CITATION LIST

Patent Literature

[PTL 1]
Japanese Unexamined Patent Application Publication No. 2007-271765
[PTL 2]
Japanese Unexamined Patent Application Publication No. 2006-271765

SUMMARY OF INVENTION

Technical Problem

In the technique of Patent Literature 2 described above, information of each layer constituting the skin is acquired by pressing the leading end of a probe against the skin, receiving reflected waves of different frequencies from the skin, and measuring the reflected waves.

However, this technique does not consider the influence of fine irregularities existing on the skin surface (skin grooves and skin hillocks). Actually, even when the leading end of the probe is pressed against the skin, the portions of the skin grooves can hardly come into contact with the leading end surface of the probe, and at the portions that are not in contact, it is not possible to accurately acquire the acoustic impedance of the horny cell layer. This problem is not limited to the measurement of skin, but also applies to the measurement of the surface of a living body such as a tooth or a nail, or the measurement of an organic or inorganic surface and/or surface layer in which fine irregularities exist.

In view of the above, it is an object of the present invention to provide a technique and a configuration for surface property measurement by which the surface properties of a substance can be accurately evaluated.

Solution to Problem

In order to solve the above-described problem, a reflection component is extracted at the maximum point in a cross-correlation function between a reflected waveform from a measurement target and a reference waveform that is a reflected waveform from a reference substance (specifically, an ultrasonic transmission medium or pure water used as a couplant), and an acoustic impedance representing the surface property is calculated according to a result of comparing the reflection component with the reference waveform.

Specifically, a surface property measurement method includes radiating an ultrasonic wave to a measurement target and acquiring a reflected signal from the measurement target;

calculating, by a measurement apparatus, a maximum value of a cross-correlation function between the reflected signal from the measurement target and a reference reflected signal from a reference substance acquired in advance;

calculating a reflection component at an interface, by using the maximum value of the cross-correlation function; and outputting, as a measurement value, one of an acoustic impedance of the measurement target or an acoustic impedance of the reference substance, according to a result of comparing the reflection component with the reference reflected signal.

Advantageous Effects of Invention

According to the above technique, a surface property of a substance can be evaluated with high accuracy.

BRIEF DESCRIPTION OF DRAWINGS

FIG. 10 illustrates a process flow when a measurement result is displayed as an image;

DESCRIPTION OF EMBODIMENTS

Hereinafter, embodiments of the present invention will be described with reference to the drawings.

Figure 1:
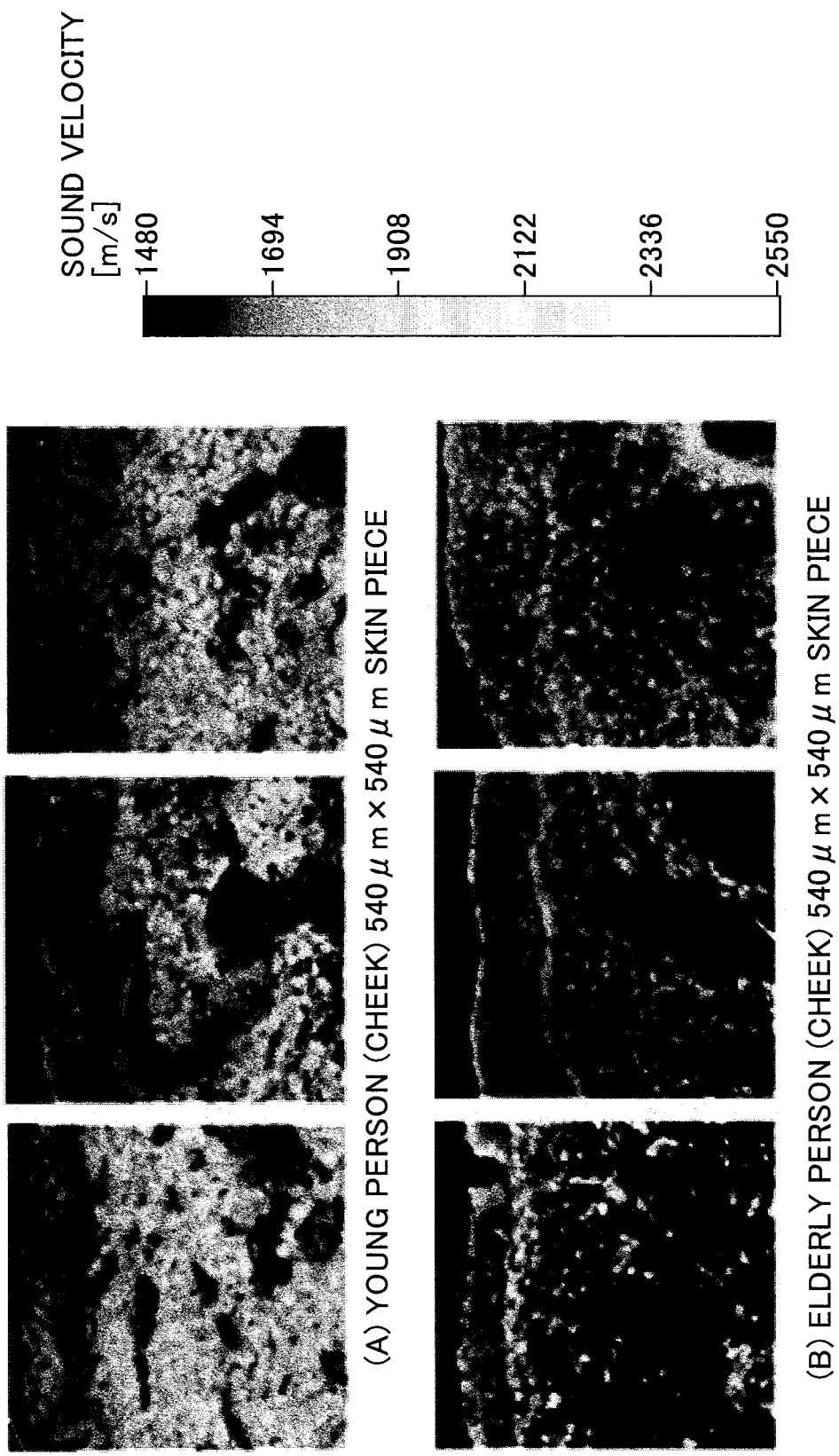
FIG. 1 is a hardness distribution image of a cross-section of skin measured by a known method (method of Patent Literature 1)
Figure 2:
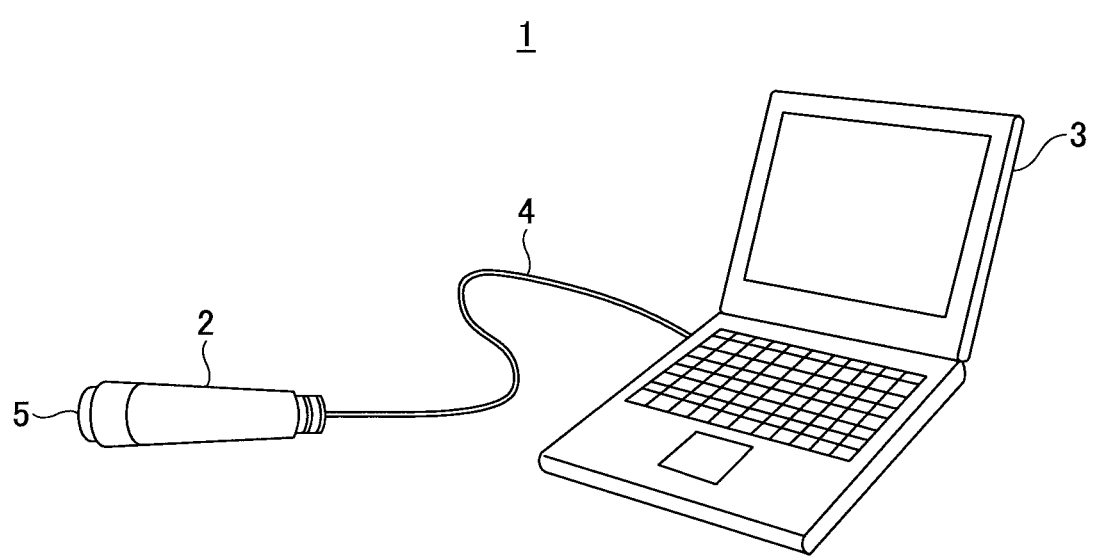
FIG. 2 is a schematic diagram of a surface property measurement apparatus according to an embodiment.

FIG. 2 is a schematic diagram of a surface property measurement apparatus 1 according to an embodiment. The surface property measurement apparatus 1 includes a probe 2 and an information processing apparatus 3. The probe 2 includes an acoustic window 5 at the leading end, through which ultrasonic waves can pass. The material of the acoustic window 5 that contacts the measurement target has a known acoustic impedance that differs from that of the measurement target, and is formed of a hard material (for example, hard resin, etc.) capable of passing ultrasonic waves.

The probe 2 can communicate with the information processing apparatus 3. In the example of FIG. 2, the probe 2 is connected by a cable 4; however, the probe 2 may be wirelessly connected. From the acoustic window 5 of the probe 2, ultrasonic waves that are two-dimensionally scanned and transmitted, are radiated to the measurement target, the reflected waves are received by the probe 2 and converted into electric signals, and the electric signals are output. The received reflected waves include information on the measurement target.

The probe 2 can be grasped by hand; for example, when measuring the skin, the probe 2 can be held by hand and directly applied to the subject's skin. Furthermore, when highly accurate measurement is desired without being affected by movement of the body, it is also possible to fix the probe 2 or fix the probe 2 and the cheek of a person together with double-sided tape.

The information processing apparatus 3 analyzes the reflected waves received by the probe 2 and detects the surface properties of the measurement target. As the information processing apparatus 3, any information processing apparatus having an arithmetic processing function and a display function can be used, such as a notebook computer and a tablet terminal, etc. In the embodiment, the information processing apparatus 3 obtains the maximum cross-correlation between the reflected waveform from the measurement target and a reference waveform, to remove the interference with the reflected waveform from internal components of the measurement target and the influence of irregularities of the surface shape (influence on the reflected waveform due to contact and non-contact with the acoustic window), and extract an accurate acoustic impedance of the surface and/or surface layer. For example, when the measurement target is skin, the accurate physical property information such as the hardness and the elasticity of the skin surface layer (horny cell layer) is acquired, upon excluding the interference from the epidermis and dermis in the skin and the influence of irregularities of the surface shape (texture and wrinkles, etc.). When the measurement target is a tooth, information such as the accurate hardness of enamel of the surface is measured, upon excluding the influence of the internal cementum and dentin and the influence of irregularities of the surface shape (roughness). When the measurement target is a multilayer film or a multilayer coating material, information such as the hardness and elasticity of the outermost layer is measured, upon reducing the influence of the inner layers and the influence of the irregularities of the surface shape.

Figure 3:
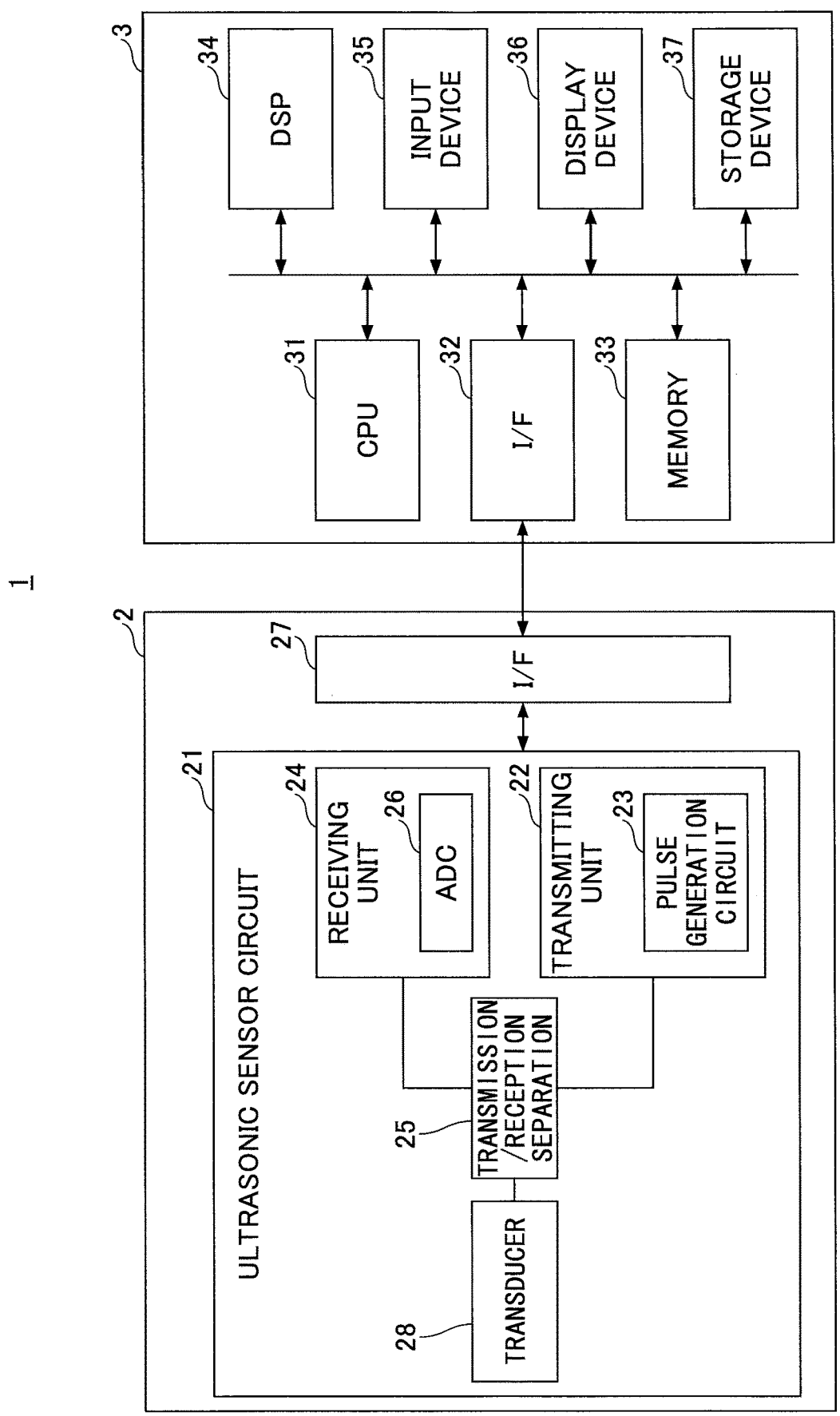
FIG. 3 is a block diagram of the surface property measurement apparatus of FIG. 2.

FIG. 3 is a block diagram of the surface property measurement apparatus 1 of FIG. 2. The probe 2 includes an ultrasonic sensor circuit 21 and an interface (I/F) 27. The interface 27 may be a wireless interface or a physical interface as described above.

The ultrasonic sensor circuit 21 includes a transmitting unit 22, a receiving unit 24, a transmission/reception separation circuit 25 that separates transmission waves and reception waves, and a transducer 28. The transmitting unit 22 includes a pulse generation circuit 23. The pulse generation circuit 23 generates a drive pulse at a predetermined timing. The transmitting unit 22 applies the drive pulse to the transducer 28 via the transmission/reception separation circuit 25. The transducer 28 converts the pulse (electric) signals into mechanical vibration and outputs ultrasonic waves.

The transducer 28 receives the reflected wave reflected from the measurement target and converts the reflected wave into an electric signal. The reception electric signal is supplied to the receiving unit 24 by the transmission/reception separation circuit 25. The receiving unit 24 detects an analog electric signal and converts the analog electric signal into a digital signal by an analog/digital converter (ADC). The digital signal (reflected wave) is transmitted to the information processing apparatus 3 via the interface 27.

The information processing apparatus 3 includes a CPU 31, an interface (I/F) 32, a memory 33, a DSP (Digital Signal Processor) 34, an input device 35, a display device 36, and a storage device 37. The reflected wave signal transmitted from the probe 2 is input to the DSP 34 via the interface 32, and the reflected wave signal is processed by the DSP 34.

The input device 35 is an input user interface such as a touch panel, a mouse, and a keyboard, etc. The display device 36 is a monitor display such as a liquid crystal display, a plasma display, and an organic EL (electroluminescence) display, etc. The storage device 37 is a hard disk drive such as a magnetic disk device or an optical disk device, and stores various programs and data. The memory 33 includes a RAM (Random Access Memory) and a ROM (Read-Only Memory), and stores the reflected waveform of the reference substance and the acoustic impedance thereof that are acquired in advance for ultrasonic measurement.

The DSP 34 determines the surface properties from the acoustic impedance of the measurement target based on the maximum cross-correlation between the reflected waveform from the measurement target and the reflected waveform from a reference substance. In the embodiment, it is assumed that the DSP 34 processes the signals of reflected ultrasonic waves. However, when using a surface property measurement program to be described later, the CPU 31 may read out the surface property measurement program stored in the storage device 37 and execute signal analysis.

Figure 4:
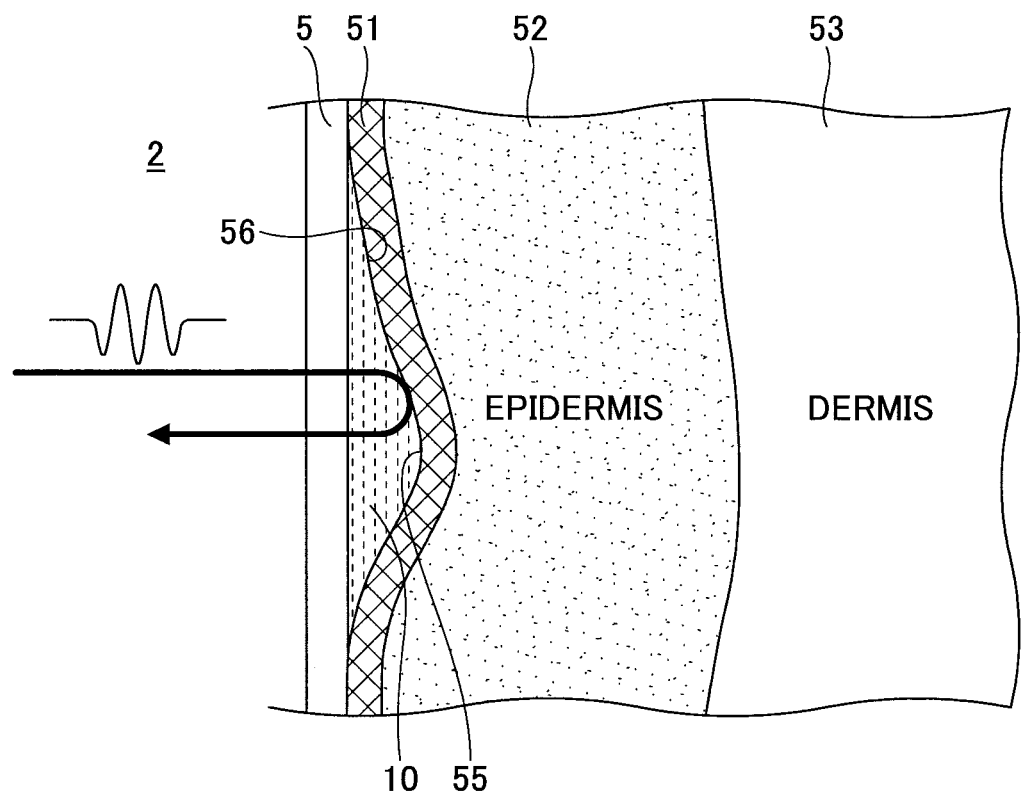
FIG. 4 is a diagram illustrating a reflection state of ultrasonic waves.

FIG. 4 is a diagram illustrating a reflection state of ultrasonic waves. For example, a case of measuring a horny cell layer 51 on the skin surface is considered. The skin is formed of epidermis 52, dermis 53, subcutaneous tissue (not illustrated), and multiple layers. The outermost surface of the epidermis 52 is the horny cell layer 51. On the surface of the skin, there are fine irregularities, that is, skin grooves 55 and skin hillocks 56. The skin grooves 55 are grooves that partition the surface of the skin into the fine skin hillocks 56; the portions of wrinkles and pores where the skin grooves are deep and roughened are also included in the skin grooves 55. Even when the acoustic window 5 of the probe 2 is pressed against the skin, in reality, the skin grooves 55 are not in contact with the acoustic window 5. Between the acoustic window 5 and the skin grooves 55, there is a couplant (ultrasonic coupling medium) 10 such as water and gel. Ultrasonic waves are almost 100% reflected in the air layer, and therefore in ultrasonic measurement, the couplant 10 is usually provided between the transducer 28 and the skin, to ensure the transmission of sound energy between the transducer 28 and the skin.

In the portions of the skin grooves 55, the acoustic window 5 cannot make direct contact with the horny cell layer 51, but contacts the couplant 10. Therefore, by the conventional method, it has been impossible to acquire accurate acoustic impedance of the horny cell layer 51. This is because the skin grooves 55 that actually exist on the skin, are treated as the skin hillocks 56. In the case of measuring the surface properties of a measurement target having fine irregularities, it is necessary to make evaluations upon distinguishing the acoustic impedance acquired at protrusions (for example, the skin hillocks 56) from the acoustic impedance acquired at the recesses (for example, the skin grooves 55).

Figure 5:
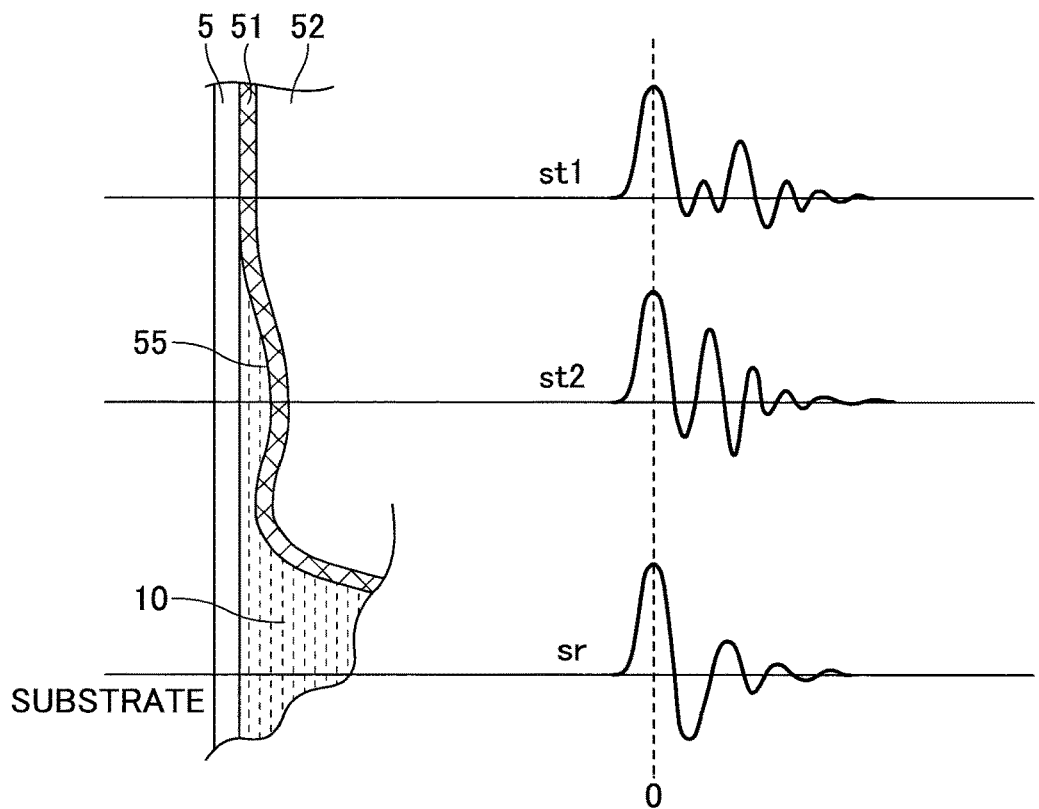
FIG. 5 is a diagram for describing the principle of the embodiment.

FIG. 5 is a diagram for describing the principle of the embodiment. In the embodiment, a reference signal representing the reflected waveform from the couplant 10 as the reference substance, and the acoustic impedance thereof, are acquired in advance. The maximum cross-correlation between the reflected waveform of the ultrasonic wave reflected by the measurement target (for example, the skin) and the reference waveform is obtained, to remove the reflection component from a layer deeper than the horny cell layer 51 on the surface, and extract the reflection information at the interface with the acoustic window 5. By comparing the reflection information with the reference signal, it is determined whether the acoustic window 5 is in direct contact with the skin, or whether the acoustic window 5 is contacting a portion of the skin groove 55 in which the couplant 10 has entered.

At a portion where the acoustic window 5 is in direct contact with the horny cell layer 51, a reflected waveform st1 is obtained. The maximum peak is a component reflected at the interface between the horny cell layer 51 and the acoustic window 5. A plurality of small peaks appearing behind the maximum peak are components reflected at portions deeper than the horny cell layer 51. For example, the components are reflected at an interface between the horny cell layer 51 and the epidermis 52, an interface between the epidermis 52 and the dermis 53 (see FIG. 4), and an interface between the dermis 53 and the subcutaneous tissue, etc.

On the other hand, at a portion where the acoustic window 5 does not contact the horny cell layer 51, a reflected waveform st2, which is different from the reflected waveform st1, is obtained. This includes the component reflected at the interface between the acoustic window 5 and the couplant 10 and the component reflected at the interface between the couplant 10 and the horny cell layer 51.

Furthermore, similar to the reflected waveform st1, the reflection component from a deeper portion of the skin is also included.

In order to obtain a reference waveform of a reflected wave from the couplant 10, the acoustic window 5 or a substrate having the same quality and the same thickness as the acoustic window 5, is brought into contact with only the couplant 10, and a reflected wave from the interface between the acoustic window 5 and the couplant 10 is acquired. This corresponds to a reference wave sr.

Figure 6:
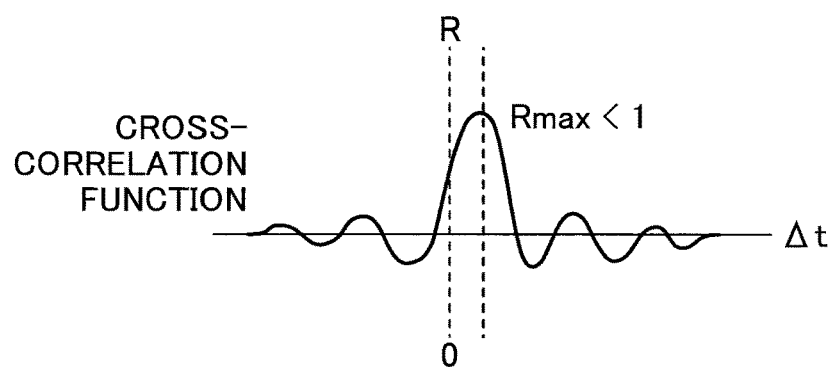
FIG. 6 is a diagram for describing a cross-correlation between a reflected waveform from a measurement target and a reference waveform.

FIG. 6 is a diagram for describing a cross-correlation function. In the embodiment, the cross-correlation function between the Fourier transform of each of the measured reflected wave and the reference wave is calculated. In FIG. 6, as a matter of convenience of description, the cross-correlation function by the waveform in the time domain before the Fourier transform, will be described.

The cross-correlation function is a value obtained by integrating the product of the reflected wave st from the measurement target and the reference wave sr, and then dividing the result of integration by the product of the effective values (rms: root-mean-square) of the waveforms, and obtaining a value from −1 to 1. Assuming that a digitally sampled waveform is a multidimensional vector, the correlation between the reflected wave st from the target and the reference wave sr is a value obtained by dividing the inner product of the vectors by the product of the absolute values. The result of calculating the correlation coefficient while changing the time difference of the waveforms, is the cross-correlation function.

In both the reference wave sr from the reference substance and the reflected wave st from the target, the reflection from the interface with the acoustic window 5 is strongest. The reflection from a portion behind (deeper than) the interface with the acoustic window 5, is smaller than the reflection from the interface with the acoustic window 5. Therefore, the point at which the cross-correlation function between the reflected wave st from the target and the reference wave sr becomes maximum, indicates the position of the interface with the acoustic window 5. The cross-correlation function at this time is expressed as Rmax.

By obtaining the maximum value of the cross-correlation function, the reflection component at a deeper part than the interface with the acoustic window 5 is removed. Note that in the case where the acoustic window 5 or the substrate is curved in a protruding shape, a deviation occurs in the position of Rmax in FIG. 6. That is, a position Δt on the time axis when the cross-correlation function becomes maximum, will not be zero.

The reflected wave st in the time domain from the measurement target is Fourier transformed, to calculate a reflected signal St in the frequency domain. Furthermore, the reference wave sr is Fourier transformed to calculate the reference signal Sr in the frequency domain. By using these signals, the magnitude of a reflection component $St^{(1)}$ at the interface when the cross-correlation function becomes maximum, is obtained. $St^{(1)}$ is calculated from equation (1).

[Equation 1]

$$S_t^{(1)} = R_m \cdot \frac{|S_t|}{|S_r|} \cdot S_r \quad (1)$$

Here, Rm is the maximum value of the cross-correlation function between the Fourier-transformed reflected signal St and the reference signal Sr, |St| is the absolute value of the reflected signal St, and |Sr| is the absolute value of the reference signal Sr.

As described above, $St^{(1)}$ is the reflection intensity at the interface where the acoustic window 5 directly contacts the substance. If the magnitudes of $St^{(1)}$ and Sr are equal, the couplant 10 directly contacts the acoustic window 5, and it can be determined that this contact portion corresponds to the portion of the skin groove 55. In this case, the acoustic impedance of the reference substance (the couplant 10) acquired in advance, is output. Note that in the present specification and claims, when the magnitudes of the reflected signal and the reference signal are "equal", it is assumed that slight errors are included due to variations in the materials of the couplant and the acoustic window, and variations in measurement conditions, etc.

When $St^{(1)}$ is lower than Sr ($St^{(1)}$<Sr), the acoustic impedance of the substance directly contacting the acoustic window 5 is higher than the acoustic impedance of the couplant 10 that is the reference substance, and therefore it can be determined that the acoustic window 5 is contacting the horny cell layer 51. In this case, the acoustic impedance of the horny cell layer 51 is calculated from the equation (2).

[Equation 2]

$$Z_t = \frac{1 - \frac{S_t}{S_r} \cdot \frac{Z_s - Z_r}{Z_s + Z_r}}{1 + \frac{S_t}{S_r} \cdot \frac{Z_s - Z_r}{Z_s + Z_r}} \cdot Z_s \quad (2)$$

Here, Zt is the acoustic impedance of horny (skin) in contact with the acoustic window 5 (or an ultrasonic radiation window), Zs is the acoustic impedance of the acoustic window, Zr is the acoustic impedance of the reference substance, St is the reflected signal after Fourier transform, and Sr is the reference signal after Fourier transform.

The obtained acoustic impedance may be converted into other dynamic properties such as volume elasticity. By converting the acoustic impedance and the dynamic property after conversion into images, it is possible to visually recognize the irregular state and elasticity of the skin surface.

Figure 7:
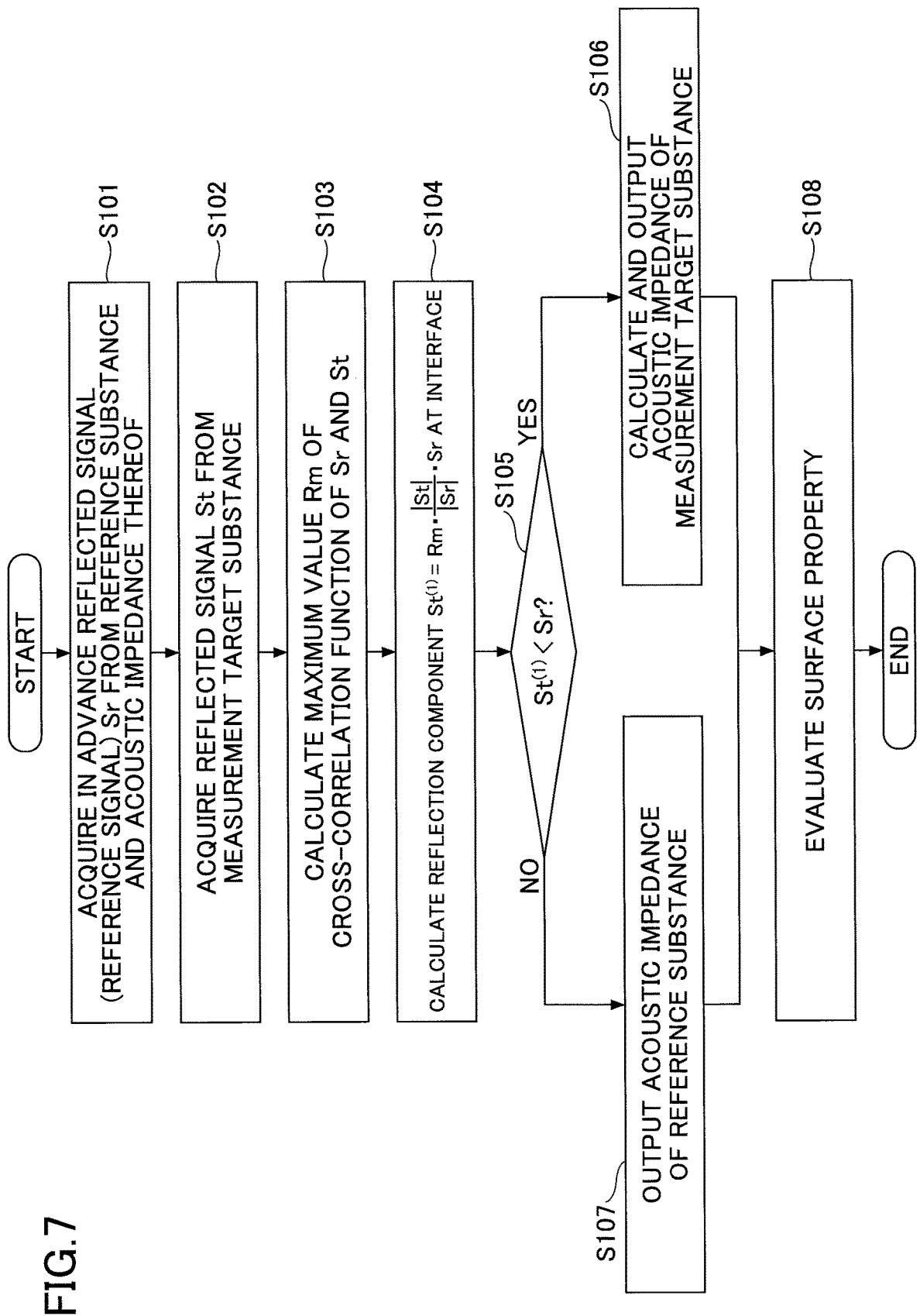
FIG. 7 is a flowchart of the surface property measurement method according to the embodiment.

FIG. 7 is a flowchart of the surface property measurement method according to the embodiment. First, the reference signal Sr representing the component reflected from the reference substance and the acoustic impedance thereof are acquired in advance (step S101). The reference signal Sr reflected from the reference substance and the acoustic impedance thereof are stored in the memory 33. As the reference substance, other than the above-described couplant 10, water and gel, etc., may be used. The reflected signal (reference signal) Sr from the reference substance is the value after the Fourier transform.

Furthermore, the reflected signal St from the measurement target is acquired (step S102). This reflected signal St is also a value after Fourier transform. Next, the maximum value Rm of the cross-correlation function between the reflected signal St and the reference signal Sr is calculated (step S103).

By using the measurement result and the calculated Rm, the reflection component $St^{(1)}$ at the interface with the acoustic window 5 is calculated (step S104). It is determined whether the reflection component $St^{(1)}$ at the interface is lower than the reference signal Sr (step S105). If the reflection component $St^{(1)}$ at the interface is lower than the reference signal Sr (YES in step S105), it means that the acoustic window 5 is actually in contact with the measurement target. In this case, the acoustic impedance of the measurement target is calculated and output (step S106).

When the reflection component $St^{(1)}$ at the interface is not lower than the reference signal Sr (NO in step S105), it means that the acoustic window 5 is in direct contact with the reference substance. In the case of the skin surface, it means that the portion corresponding to the skin groove 55 is being measured. In this case, the acoustic impedance of the reference substance is output (step S107). Once the acoustic impedance is obtained over a predetermined range, the surface properties are evaluated (step S108), and the process is ended.

By the above method, it is possible to accurately measure and evaluate fine irregularities and dynamic properties of the surface, by measuring surface properties using ultrasonic waves. For example, as the evaluation of the skin surface of a person, the age by decade of the person to which the skin state corresponds, can be evaluated, based on the fineness of texture, the smoothness, and the elasticity, etc.

Figure 8:
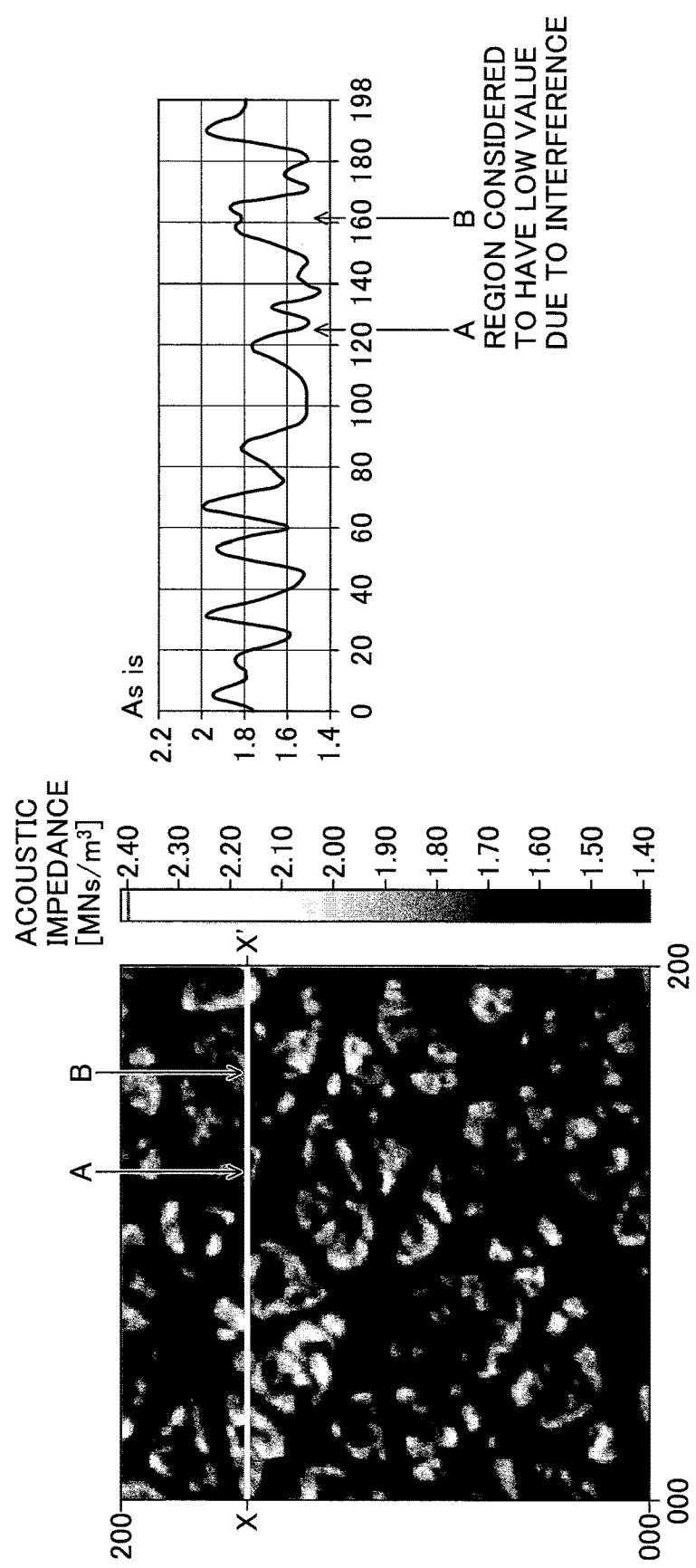
FIG. 8 illustrates a measurement result when the cross-correlation between the reflected wave from the target and the reference wave is not used.

FIG. 8 illustrates an ultrasonic image of the living human skin and the acoustic impedance on a line X-X', when the cross-correlation between the reflected wave from the target and the reference wave is not used. The horizontal axis of the image is the length (μm) and the vertical axis is the acoustic impedance ($Pa·s/m^3$).

Figure 9:
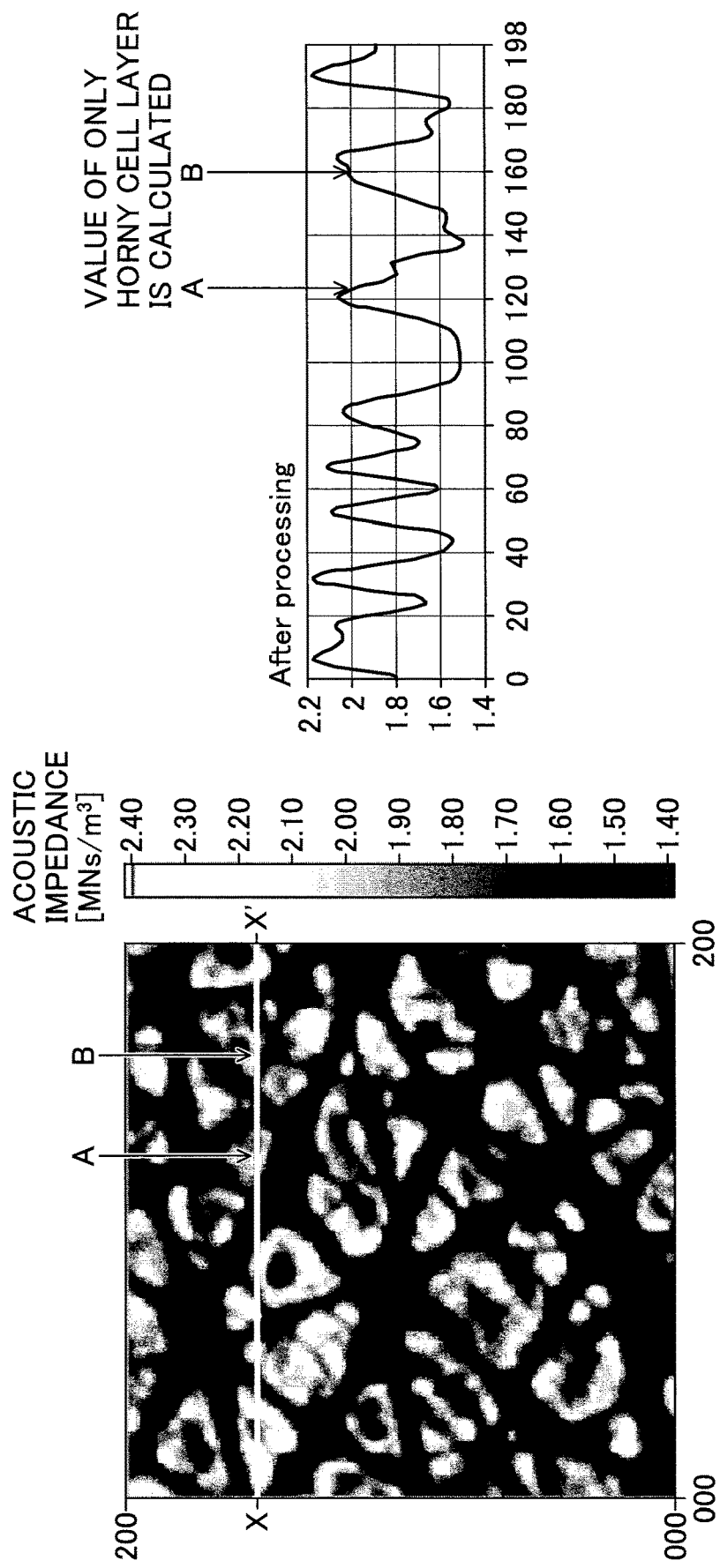
FIG. 9 illustrates a measurement result when the cross-correlation between the reflected wave from the target and the reference wave is used.

FIG. 9 illustrates an ultrasonic image and the acoustic impedance on the line X-X' when applying the technique of the above-described embodiment to the same sample as that of FIG. 8.

Both FIG. 8 and FIG. 9 illustrate acoustic impedance images of the two-dimensional profile of skin on the forearm inner side (flexion side) of a healthy 20-year-old male. The skin was measured after washing and then drying for a certain period of time. For the measurement, a transducer of 40 MHz to 120 MHz was used, ultrapure water was used for the couplant, and an acrylic plate was used for the substrate with which the skin was brought into contact. Focusing on the wavelength most reflected by the surface, images were acquired at 200×200 pixels.

In the conventional method illustrated in FIG. 8, reflections from the inner layers show as interference at the points A and B on the line X-X', resulting in low values. On the other hand, in the method of FIG. 9, the reflection components from the inside were removed and the value of only the horny cell layer 51 was calculated. As described above, by the method according to the embodiment, the surface irregularity information can be accurately acquired.

FIG. 10 illustrates a process flow when the acquired acoustic impedance is displayed as image information. This process can also be performed by the DSP 34 or the CPU 31 of the information processing apparatus 3. The same steps as those in FIG. 7 are denoted by the same reference numerals. First, a reflected signal (Fourier transformed signal) Sr from the reference substance and the acoustic impedance thereof are acquired in advance (step S101). Coordinate data of measurement points at the time of relatively scanning the ultrasonic waves with respect to the measurement target, is acquired (step S201). In the relative scanning, the probe 2 may be scanned with respect to a fixed measurement target, or the ultrasonic sensor circuit 21 may be fixed and a stage holding the sample may be two-dimensionally driven.

Next, the acoustic impedance at each measurement point is acquired (step S202). The acoustic impedance of the target or the acoustic impedance of the reference substance is acquired by comparing the interface reflection intensity and the reference signal intensity based on the maximum cross-correlation function between the Fourier-transformed reference signal and the reflected signal from the target, as in S102 to S107 in FIG. 7. Image data is generated with gradation or color according to the acoustic impedance (step S203).

It is determined whether there are other measurement points (step S204). If there is another measurement point (YES in S204), steps S201 to S203 are repeated. Upon completion of the processes of steps S201 to S203 for all measurement points (YES in S204), the image is displayed (step S205).

In the above flow, once the reflected wave and the Fourier transform value thereof are stored in association with the coordinate value in the memory 33 for all of the measurement points, the acoustic impedance at each coordinate point may be calculated. In this case also, if image data is generated for all coordinate points, the image is displayed on the display device 36. Furthermore, the acoustic impedance may be converted into another dynamic property and displayed in gradation or color according to the conversion value.

According to the above method, it is possible to accurately measure the surface properties by distinguishing between the horny cell layer 51 actually contacting the acoustic window 5 and the portion corresponding to the skin groove 55, and excluding the reflection components from the inner layer.

FIGS. 11A to 11D are images illustrating the state of the skin surface actually measured by using the surface property measurement apparatus 1 according to the embodiment. The skin surfaces of the cheeks of 70 females in their 20 s to 80 s were measured. The breakdown of the 70 females was 19 females in their 20 s (20-29 years old), 15 females in their 40 s (40-49 years old), 19 females in their 60 s (60-69 years old), and 17 females in their 70 s and 80 s (70-86 years old).

As a measurement method, this time, in order to eliminate the influence of the movement of the body and to obtain a more accurate value, the probe 2 was fixed vertically such that the acoustic window 5 was horizontal. The probe 2 was arranged such that the cheek of the measured person horizontally contacts the acoustic window 5, the leading end of the probe 2 of the surface property measurement apparatus 1 was pressed against the cheek, ultrasonic waves were radiated onto the skin of the measurement target region, the reflected signals from the measurement target region were acquired, and the acoustic impedance was calculated. The acoustic window 5 of the probe 2 was formed of acrylic having a thickness of 0.5 mm. Physiological saline was applied as a couplant to the measured person's cheek in advance. The measurement was carried out under constant conditions of a humidity of 45% and a temperature of 25° C.

FIGS. 11A to 11D illustrate the results of selecting a representative example of an acoustic impedance distribution of each measurement group (20 s, 40 s, 60 s, and 80 s). The portions with high acoustic impedance (the white portions and the light-color portions) in the image are skin, the portions with low acoustic impedance (the black portions and the dark-color portions) in the image bubbles and couplant. The reflected signals from the measurement region were cross-correlated with previously acquired reference reflected signals of the reference substance (physiological saline), and the reflection component at the interface was calculated with the maximum value of the cross-correlation function as an index, to calculate the acoustic impedance. The calculated acoustic impedance indicates an accurate measurement result from which the interference component caused by internal reflection has been removed.

Figure 11A:
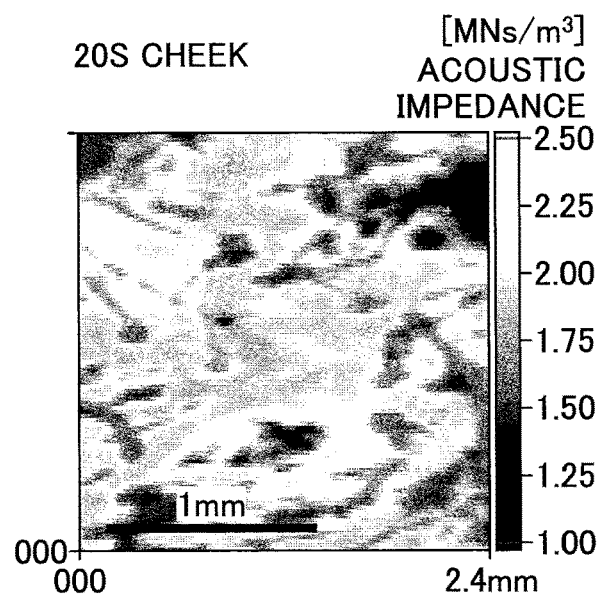
FIG. 11A is an image illustrating the state of the skin surface actually measured by using the surface property measurement apparatus according to the embodiment.
Figure 11B:
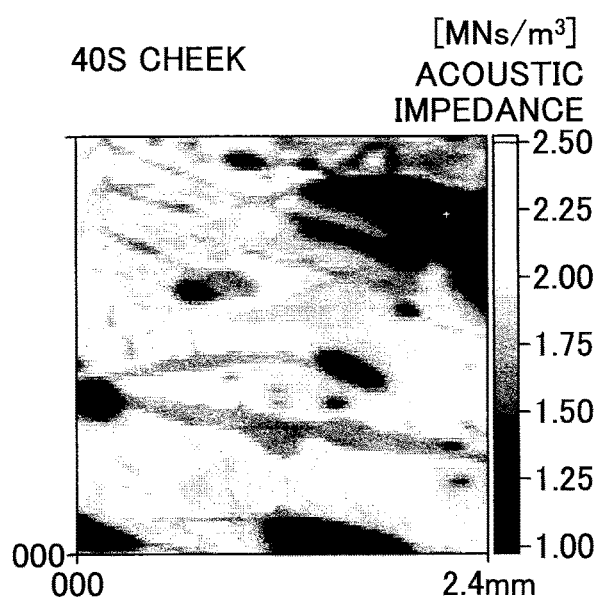
FIG. 11B is an image illustrating the state of the skin surface actually measured by using the surface property measurement apparatus according to the embodiment.
Figure 11C:
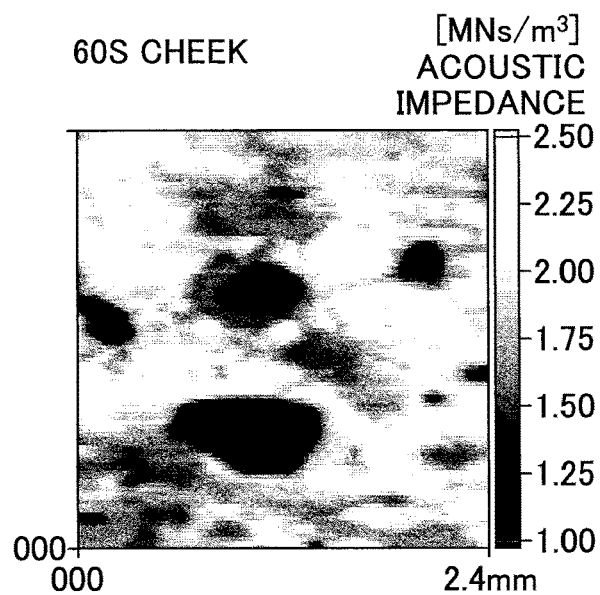
FIG. 11C is an image illustrating the state of the skin surface actually measured by using the surface property measurement apparatus according to the embodiment.
Figure 11D:
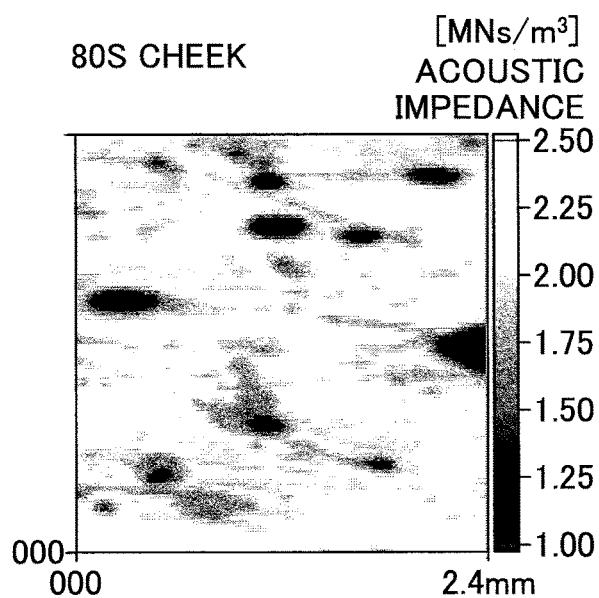
FIG. 11D is an image illustrating the state of the skin surface actually measured by using the surface property measurement apparatus according to the embodiment.

It can be seen that as age increases, the impedance in the image turns white (high impedance). In the skin of the females in their 20 s in FIG. 11A, the impedance distribution is uniform overall. This indicates that the hillocks rise equally with elasticity and the texture is fine. In FIG. 11B to FIG. 11D, as age increases as the 40 s, the 60 s, and the 80 s, the high-impedance portions increase. This is considered to be due to the thickening of the horny cell layer and the roughening of the texture with aging. Furthermore, locally low impedance portions exist in the skin of the 40 s and the 60 s because the acoustic impedance is low as the couplant enters wrinkles and cracks due to the thickening of the horny cell layer. In this way, from the measurement result of the skin surface using the acoustic impedance, not only is it possible to obtain the accurate acoustic impedance value of the horny cell layer excluding the influence of irregularities and the influence inside the skin, but it is also possible to obtain information regarding on the fineness and smoothness of the skin.

Figure 12:
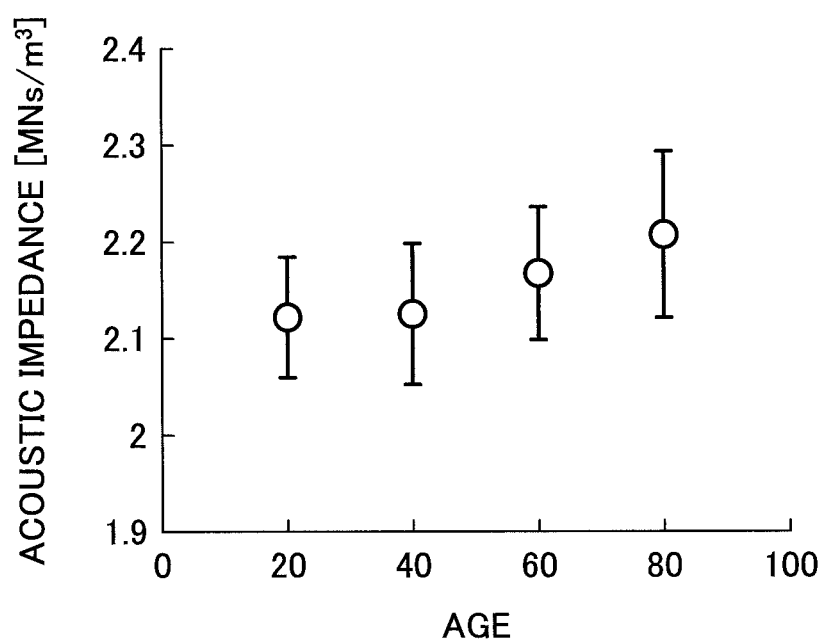
FIG. 12 illustrates the average acoustic impedance by age based on the measurement data of FIGS. 11A to 11D.

FIG. 12 illustrates the average acoustic impedance by age based on the measurement results of FIGS. 11A to 11D. Among the four groups, the average acoustic impedance of 20 s (20 to 29 years old) is indicated at age "20". The average acoustic impedance of the 40 s (40 to 49 years old) is indicated at age "40". The average acoustic impedance of 60 s (60-69 years old) is indicated at age "60". The acoustic impedance of the 70 s and the 80 s (70-86 years old) is the age "80". As age increases, the acoustic impedance tends to be higher, and the relationship between aging and the hardening of the horny cell layer can be inferred.

As illustrated in FIGS. 11A to 11D, by acquiring the average acoustic impedance distribution for each age group in advance, the skin age of the measured person can be estimated. The skin age may or may not match the actual age. If the measured skin age is higher than the actual age, measures can be recommended according to the degree of the difference.

As described above, by using the configuration and the technique of surface property measurement according to the embodiment, surface properties can be evaluated (step S108 in FIG. 7) with increased accuracy.

When the above method is implemented by the surface property measurement program, the surface property measurement program is stored in advance in the memory 33 or the storage device 37, and the CPU 31 reads out the surface property measurement program and executes the surface property measurement program.

The surface property measurement program causes the CPU 31 to execute (a) a procedure of acquiring a reflected signal of an ultrasonic wave radiated to a measurement target;

(b) a procedure of calculating a maximum value of a cross-correlation function between the reflected signal from the measurement target and a reference reflected signal from a reference substance acquired in advance;

(c) a procedure of calculating a reflection component at an interface of the measurement target, by using the maximum value of the cross-correlation function; and (d) a procedure of outputting, as a measurement value, one of an acoustic impedance of the measurement target or an acoustic impedance of the reference substance, according to a result of comparing the reflection component with the reference reflected signal. Accordingly, a surface property can be evaluated with high accuracy.

The present international patent application claims the benefit of priority of Japanese Priority Patent Application No. 2015-192075, filed on Sep. 29, 2015 to the Japanese patent office, and Japanese Priority Patent Application No. 2016-175317, filed on Sep. 8, 2016 to the Japanese patent office, the contents of which are incorporated herein by reference in their entirety.

INDUSTRIAL APPLICABILITY

According to the present invention, the hardness information of the surface of a specimen or a sample can be measured with high accuracy, and therefore the present invention can be used for evaluating the dynamic properties of the living body surface such as the skin, hair, nails, and teeth, and the physical properties and the presence or absence of defects of an organic or inorganic surface and/or surface layer.

REFERENCE SIGNS LIST 1 surface property measurement apparatus
2 probe
3 information processing apparatus
5 acoustic window
21 ultrasonic sensor circuit
31 CPU (processor)
33 memory
34 DSP (signal processing unit)
37 storage device

The invention claimed is:

1. A surface property measurement method comprising:
   radiating an ultrasonic wave to a measurement target and acquiring a reflected signal from the measurement target;
   calculating, by a measurement apparatus, a maximum value of a cross-correlation function between the reflected signal from the measurement target and a reference reflected signal from a reference substance acquired in advance;
   calculating a reflection component at an interface, by using the maximum value of the cross-correlation function;
   outputting, as a measurement value, one of an acoustic impedance of the measurement target or an acoustic impedance of the reference substance, according to a result of comparing the reflection component with the reference reflected signal, and
   outputting the acoustic impedance of the reference substance, upon determining that an intensity of the reflection component is not lower than an intensity of the reference reflected signal.

2. The surface property measurement method according to claim 1, further comprising:
   calculating and outputting the acoustic impedance of the measurement target, upon determining that an intensity of the reflection component is lower than an intensity of the reference reflected signal.

3. The surface property measurement method according to claim 1, wherein the calculating of the reflection component includes multiplying the reference reflected signal by a ratio of the reflected signal from the measurement target to the reference reflected signal and by the maximum value of the cross-correlation function.

4. The surface property measurement method according to claim 1, further comprising:

one-dimensionally or two-dimensionally and relatively scanning the ultrasonic wave to the measurement target; and outputting the measurement value for each coordinate point.

5. The surface property measurement method according to claim 1, wherein the radiating of the ultrasonic wave includes radiating the ultrasonic wave upon bringing an acoustic window of a probe of the measurement apparatus in contact with the measurement target.

6. The surface property measurement method according to claim 1, wherein the reference substance is water or a gelatinous substance.

7. The surface property measurement method according to claim 1, wherein
the measurement target is skin, and wherein
the surface property measurement method further comprises:
evaluating at least one of elasticity, texture, pores, and wrinkles of the skin, based on the measurement value.

8. The surface property measurement method according to claim 1, wherein
the measurement target is an organic or inorganic, single-layered or multilayered substance, and wherein
the surface property measurement method further comprises:
evaluating at least one of surface roughness, elasticity, and defects of an outermost layer of the measurement target, based on the measurement value.

9. A non-transitory computer-readable recording medium storing a surface property measurement program that causes a computer to execute a process, the process comprising:
acquiring a reflected signal of an ultrasonic wave radiated to a measurement target;
calculating a maximum value of a cross-correlation function between the reflected signal from the measurement target and a reference reflected signal from a reference substance acquired in advance;
calculating a reflection component at an interface, by using the maximum value of the cross-correlation function;
outputting, as a measurement value, one of an acoustic impedance of the measurement target or an acoustic impedance of the reference substance, according to a result of comparing the reflection component with the reference reflected signal, and
outputting the acoustic impedance of the reference substance, upon determining that an intensity of the reflection component is not lower than an intensity of the reference reflected signal.

10. A surface property measurement apparatus comprising:
an ultrasonic wave transmitting/receiving unit configured to radiate an ultrasonic wave to a measurement target and receive a reflected signal from the measurement target;
a memory configured to store an intensity of a reference reflected signal from a reference substance measured in advance, and an acoustic impedance of the reference substance; and
a signal processing unit configured to calculate a reflection component at an interface, based on a maximum value of a cross-correlation function between the reflected signal from the measurement target and the reference reflected signal, and output, as a measurement value, one of an acoustic impedance of the measurement target or the acoustic impedance of the reference substance, according to a result of comparing the reflection component with the reference reflected signal,
wherein the signal processing unit reads, from the memory, and outputs the acoustic impedance of the reference substance, upon determining that an intensity of the reflection component is not lower than the intensity of the reference reflected signal.

11. The surface property measurement apparatus according to claim 10, wherein the signal processing unit calculates and outputs the acoustic impedance of the measurement target, upon determining that an intensity of the reflection component is lower than the intensity of the reference reflected signal.

* * * * *